(12) United States Patent
Li et al.

(10) Patent No.: US 12,092,592 B2
(45) Date of Patent: Sep. 17, 2024

(54) DEVICE AND METHOD FOR MEASURING THE RELATIVE PERMEABILITY OF PROPPED FRACTURES IN SHALE CONSIDERING PROBABILITY DISTRIBUTION

(71) Applicant: Southwest Petroleum University, Chengdu (CN)

(72) Inventors: Zhenglan Li, Chengdu (CN); Yonggang Duan, Chengdu (CN); Mingqiang Wei, Chengdu (CN); Quantang Fang, Chengdu (CN); Le Luo, Chengdu (CN); Keyi Ren, Chengdu (CN); Lei Meng, Chengdu (CN); Shuxin Li, Chengdu (CN); Zhihong Nie, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 130 days.

(21) Appl. No.: 18/148,661

(22) Filed: Dec. 30, 2022

(65) Prior Publication Data
US 2024/0159692 A1      May 16, 2024

(30) Foreign Application Priority Data
Nov. 5, 2022   (CN) .......................... 202211380300

(51) Int. Cl.
*G01N 15/08* (2006.01)
*G01N 23/046* (2018.01)
(Continued)

(52) U.S. Cl.
CPC ....... *G01N 23/046* (2013.01); *G01N 15/0806* (2013.01); *G01N 15/082* (2013.01);
(Continued)

(58) Field of Classification Search
CPC . G01N 23/046; G01N 15/082; G01N 15/0826
See application file for complete search history.

(56) References Cited

U.S. PATENT DOCUMENTS 5,311,766 A * 5/1994 Persoff ............... G01N 15/0826
                                                          73/38
9,183,326 B2 * 11/2015 de Prisco ................. G06F 30/20
2019/0226970 A1 * 7/2019 Dusterhoft .............. E21B 43/26

FOREIGN PATENT DOCUMENTS

CN    104498071 A    4/2015
CN    106869911 A    6/2017
(Continued)

*Primary Examiner* — Lam S Nguyen
(74) *Attorney, Agent, or Firm* — Nitin Kaushik

(57) ABSTRACT

The present invention discloses a device and method for measuring the relative permeability of propped fractures in shale considering probability distribution, comprising a gas cylinder, a water pump, a booster pump, a rock slab holder, a differential pressure sensor, a directional X-ray source, an X-ray detector, an X-ray shielding box, a tee, a liquid meter, a gas meter, an electronic balance, and a vacuum pump; the inlet of rock slab holder is respectively connected with the gas cylinder and the water pump by the pipe, the outlet is connected with the liquid meter and the vacuum pump by the tee, and the differential pressure sensor is connected with both ends of the rock slab holder; the booster pump is connected with the rock slab holder by the pipe; the inlet of the gas meter is connected with the liquid meter, and the outlet is connected to the external atmosphere.

7 Claims, 5 Drawing Sheets

(51) Int. Cl.
*G01N 23/083* (2018.01)
*G01N 33/24* (2006.01)
(52) U.S. Cl.
CPC ........... *G01N 23/083* (2013.01); *G01N 33/24* (2013.01); *G01N 2223/04* (2013.01); *G01N 2223/419* (2013.01); *G01N 2223/616* (2013.01)

(56) References Cited

FOREIGN PATENT DOCUMENTS

| | | |
|---|---|---|
| CN | 107120110 A | 9/2017 |
| CN | 212748663 U | 3/2021 |
| CN | 114135271 A | 3/2022 |

* cited by examiner

DEVICE AND METHOD FOR MEASURING THE RELATIVE PERMEABILITY OF PROPPED FRACTURES IN SHALE CONSIDERING PROBABILITY DISTRIBUTION

CROSS-REFERENCE TO RELATED APPLICATIONS

The application claims priority to Chinese patent application No. 202211380300.8, filed on Nov. 5, 2022, the entire contents of which are incorporated herein by reference.

TECHNICAL FIELD

The present invention pertains to a device and method for measuring the relative permeability of propped fractures in shale considering probability distribution, belonging to the technical field of petrophysical experiments.

BACKGROUND

The extremely low permeability of shale increases the difficulties in measuring the gas-water relative permeability curve of pure shale matrix. Most of the existing shale relative permeability curves are measured in the presence of fractures. The test results are a comprehensive reflection of the relative permeability of fractures and matrix. Fracture density affects the results of the relative permeability curves, so it is necessary to measure the relative permeability curves of fractures and matrix separately. How to distinguish the flow in fractures from the flow in matrix and obtain the relative permeability curve in fractures is greatly significant for the numerical simulation in shale gas reservoir, the study on fracturing fluid flowback law and the study on gas-water flow law.

The existing methods for testing shale relative permeability are disadvantaged by the following problems: 1) the shale matrix permeability is low and it takes a long time to be fully saturated with water, 2) due to small pore size and high capillary pressure of shale, the method for measuring the relative permeability based on water flooding is easily affected by imbibition, and it is difficult to calculate water saturation in fractures independently, 3) it takes a long time for the steady-state method to reach the specified saturation, while the non-steady-state method is affected by the fracture, and it is difficult to accurately measure the water saturation changed rapidly in the fractures at the initial stage, and 4) Due to the effect of proppant displacement and irregular flow channels in the fractures, the flow of gas and water may be locally unstable and turbulent. Even if the average water saturation in the propped fracture is the same, the flow capacity of the gas or water may vary greatly. Therefore, from the perspective of accurate measurement of fracture water saturation and effective calculation of relative permeability, there is a need to establish a methodology to separately distinguish fluids in fractures, and use the $R^{th}$ percentile to characterize fracture relative permeability affected by turbulence at the same saturation, so as to obtain the curves of fracture relative permeability rapidly.

SUMMARY

To overcome the problems in the prior art, the present invention provides a device and method for measuring the relative permeability of propped fractures in shale considering probability distribution.

The technical solutions provided by the present invention to solve the above technical problems are: a device for measuring the relative permeability of propped fractures in shale considering probability distribution, comprising a displacement system, a CT scanning imaging system and a metering system;

The displacement system comprises a gas cylinder, a water pump, a booster pump, a rock slab holder, and a differential pressure sensor; the CT scanning imaging system comprises a directional X-ray source, an X-ray detector, and an X-ray shielding box; the measuring system comprises a tee, a liquid meter, a gas meter, an electronic balance, and a vacuum pump;

The inlet of rock slab holder is respectively connected with the gas cylinder and the water pump by the pipe, the outlet is connected with the liquid meter and the vacuum pump by the tee, and the differential pressure sensor is connected with both ends of the rock slab holder; the booster pump is connected with the rock slab holder by the pipe;

The directional X-ray source, the X-ray detector, the rock slab holder, and the electronic balance are all placed in the X-ray shielding box, the rock slab holder is placed on the electronic balance and located between the directional X-ray source and the X-ray detector;

The inlet of the gas meter is connected with the liquid meter, and the outlet is connected to the external atmosphere.

A further technical solution is that the gas source control valve, the gas flow meter and the gas pressure sensor are installed between the gas cylinder and the rock slab holder.

A further technical solution is that the liquid pressure sensor is installed between the water pump and the rock slab holder.

A further technical solution is that the pressure gauge and the confining pressure control valve are installed between the pressure pump and the rock slab holder.

A further technical solution is that the pressure gauge and the vacuum control valve are installed between the vacuum pump and the tee.

A further technical solution is that the outlet control valve is installed at the outlet of the gas meter.

A further technical solution is that the position adjustment slide is also installed in the X-ray shielding box, and the directional X-ray source and the X-ray detector are respectively installed at both ends of the position adjustment slide.

A method for measuring relative permeability of shale fractures considering probability distribution, specifically comprising the following steps:

Step 1: Prepare two cuboid shale slabs of the same size, stack them together, and lay proppants on the contact surface;

Step 2: Put the whole shale slab into the rock slab holder, apply confining pressure on the upper, lower and left and right sides of the slab with the booster pump, and measure the mass (denoted as $m_1$) of the shale sample with proppant by the electronic balance;

Step 3: Turn on the directional X-ray source, adjust CT scanning parameters according to the shale rock slab size and the fracture size and determine a set of appropriate scanning parameters;

Step 4: Determine the attenuation coefficient of pure substance with scanning parameters set in Step 3;

The rock slab holder is filled with air and pressurized to the specified fluid pressure, the CT projection images of pure air are obtained continuously after the pressure is stabilized, and the X-ray projection result of pure air is obtained by averaging multiple projection images, which is denoted as projection image A. Then, the same measurement is conducted for the gas and liquid used in relative permeability test and the standard block made of the same material as the proppant respectively, and the corresponding X-ray projection results are obtained, denoted as projection image B, projection image C and projection image D respectively. Next the difference of attenuation coefficients of pure substances is calculated by the following equation.

$$(\mu_{gas} - \mu_{air})L = -\ln\frac{I_B}{I_A}$$

$$(\mu_{liquid} - \mu_{air})L = -\ln\frac{I_C}{I_A}$$

$$(\mu_{proppant} - \mu_{air})L = -\ln\frac{I_D}{I_A}$$

Where, $I_A$, $I_B$, $I_C$ and $I_D$ are the intensity of each pixel point in the projection images A, B, C and D, respectively; L is the inner length of the holder cavity; $\mu_{air}$, $\mu_{gas}$, $\mu_{liquid}$ and $\mu_{proppant}$ stand for the attenuation coefficients of X-ray passing through air, experimental gas, experimental liquid and proppant successively;

Step 5: Put the whole shale slab into the rock slab holder, and apply confining pressure on the upper, lower and left and right sides of the slab with the booster pump; inject air and pressurize to the fluid pressure p required for the relative permeability experiment; acquire the CT projection images continuously after the pressure is stabilized, average multiple projection images to obtain the X-ray projection result of the rock slab, and record it as projection image E;

Step 6: Calculate the porosity and pore volume in the propped fractures of the shale rock slab;

$$(\mu_{proppant} - \mu_{air})\phi L = -\ln\frac{I_E}{I_A}$$

Where, L is the inner length of the holder cavity; $\phi$ is the porosity; $I_E$ is the intensity of each pixel point in the projected image E;

$$V_p - \sum_j A\phi_j L$$

Where, A is the area of a single pixel in the projection image; $\phi_j$ is the calculated porosity at each pixel point; $V_p$ is the void volume in the propped fracture;

Step 7: Turn on the directional X-ray source, adjust the flow rates of the flow meter and the water pump, inject gas and water into the rock slab in a certain proportion, and record the following data per second for a period of time: projection image of shale rock, the gas rate $q_g$ at the outlet, the water rate $q_w$, pressure $p_1$ at the holder inlet, the pressure difference $\Delta p$ between the two ends of the rock slab, and the reading m of the electronic balance; Change the gas-water injection ratio and repeat Step 7. The injection process of each proportion is maintained for the same time;

Step 8: Calculate the saturation and permeability at each moment under various gas-water injection ratios;

The water saturation at each pixel point in the projection image at each moment is calculated by the following equation:

$$[(\mu_{proppant} - \mu_{gas})(1 - \phi) + (\mu_{liquid} - \mu_{gas})\phi s_w]L = -\ln\frac{I_t}{I_B}$$

The overall average water saturation in the fracture is calculated by the following equation:

$$\overline{s_w} = \frac{V_w}{V_p} = \frac{\sum_j A\phi_j s_{wj} L}{\sum_j A\phi_j L} = \frac{\sum_j \phi_j s_{wj}}{\sum_j \phi_j}$$

The mass of water imbibed into matrix can be calculated by the following equation:

$$m_w = m - m_1 - \rho\sum_j A\phi_j s_{wj} L$$

Effective permeability of gas and water at corresponding time:

$$K_{ge} = \frac{2p_a \cdot q_g \cdot \mu_g \cdot l}{A(p_1^2 - p_a^2)}$$

$$K_{we} = \frac{q_w \cdot \mu_w \cdot l}{A\Delta p}$$

Where, $K_{ge}$ is the effective permeability of gas; $K_{we}$ is the effective permeability of liquid; $p_a$ is atmospheric pressure; $p_1$ is the pressure at the inlet; $q_g$ is gas flow rate; $q_w$ is liquid flow rate; l is the length of propped fracture; A is the sectional area of the fracture; $\mu_g$ and $\mu_w$ are gas and liquid viscosity at the test temperature and pressure, respectively;

The relative permeability of gas and water is calculated by the following equation:

$$K_{rg} = \frac{K_{ge}}{K_g}$$

$$K_{rw} = \frac{K_{we}}{K_g}$$

Where, $K_g$ is the effective permeability of pure gas; $k_{rg}$ and $k_{rw}$ are the relative permeability of gas and water respectively;

Step 9: Calculate the fracture relative permeability curve considering the probability distribution according to the saturation and permeability at each time.

A further technical solution is that Step 9 specifically comprises:

Step 9-1: Count the gas phase relative permeability value $K_{rg}$ under the same water saturation $\overline{s_w}$ at all times, and work out a frequency distribution histogram of $K_{rg}$; calculate the gas relative permeability values corresponding to the $R^{th}$ percentile; similarly, work out the water relative permeability values corresponding to the $R^{th}$ percentile;

Step 9-2: Repeat Step 9-1 with different water saturation $\overline{s_w}$, and count the relative permeability values of gas and water corresponding to each $R^{th}$ percentile at different water saturations;

Step 9-3: Based on the relative permeability values of gas and water corresponding to different water saturations under the same $R^{th}$ percentile, the fracture relative permeability curve considering probability distribution can be obtained.

The present invention has the following beneficial effects:

I. The water volume in fractures and matrix can be measured respectively, so as to accurately calculate the water saturation in propped fractures;

II. In consideration of the relative permeability fluctuation caused by unsteady turbulence of gas and liquid in the propped fracture, the relative permeability curves with different probabilities can be characterized by $R^{th}$ percentile;

III. With CT projection data instead of reconstructed data, second-level image acquisition can be realized so as to track the change of water saturation quickly and improve the test efficiency;

IV. There is no need to be fully saturated or wait for the flow to be stable, greatly reducing the time for shale relative permeability testing.

EXPLANATION OF NUMBERS MARKED IN THE FIGURE

1—gas cylinder, 2—gas source control valve, 3—gas flow meter, 4—gas pressure sensor, 5—water pump, 6—liquid pressure sensor, 7—directional X-ray source, 8—rock slab holder, 9—differential pressure sensor, 10—X-ray detector, 11—electronic balance, 12—confining pressure control valve, 13—pressure gauge, 14—booster pump, 15—position adjustment slide, X-ray shielding box, 17—liquid meter, 18—gas meter, 19—outlet control valve, 20—vacuum control valve, 21—metering control valve, 22—pressure gauge, 23—vacuum pump.

DETAILED DESCRIPTION OF THE EMBODIMENTS

The technical solutions of the embodiments of the present invention will be described expressly and integrally in conjunction with the appended figures of the embodiments of the present invention. It is clear that the described embodiments are some but not all of the embodiments of the present invention. According to the embodiments of the present invention, all other embodiments obtained by those of ordinary skill in the art without creative effort fall within the protection scope of the present invention.

Figure 1:
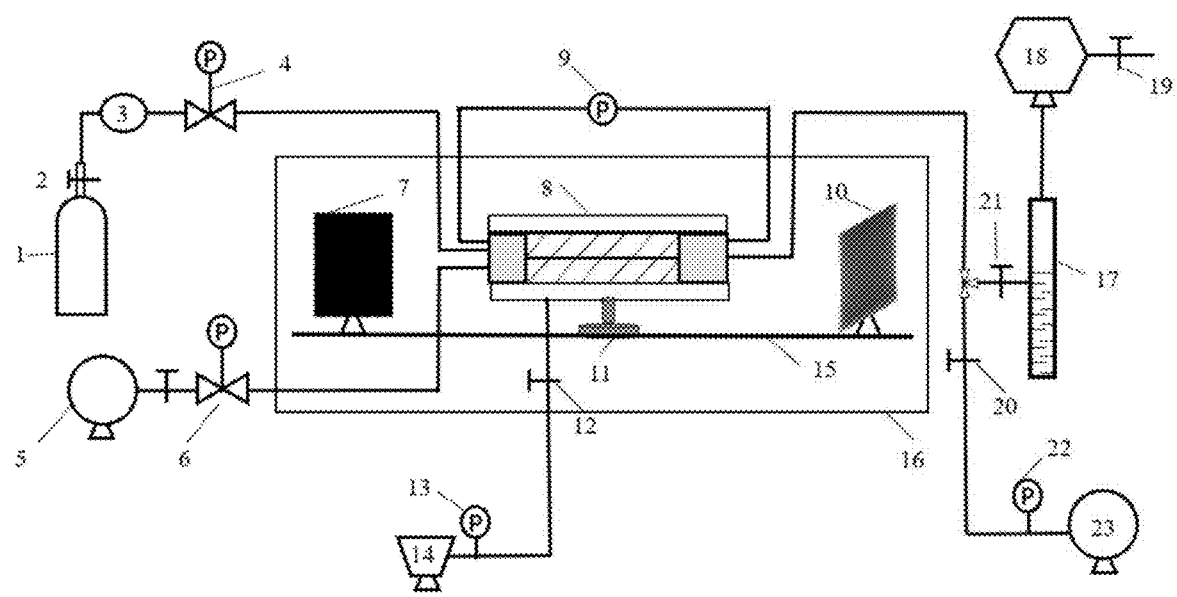
FIG. 1 is a structure diagram of the relative permeability measuring device for shale fractures.

As shown in FIG. 1, the device for measuring the relative permeability of propped fractures in shale considering probability distribution in the present invention comprises a displacement system, a CT scanning imaging system and a metering system;

The displacement system comprises a gas cylinder (1), a gas source control valve (2), a gas flow meter (3), a gas pressure sensor (4), a water pump (5), a liquid pressure sensor (6), a booster pump (14), a pressure gauge (13), a confining pressure control valve (12), a rock slab holder (8), and a differential pressure sensor (9) and connecting pipe;

The CT scanning imaging system comprises an X-ray shielding box (16), a directional X-ray source (7) placed in the X-ray shielding box (16), an X-ray detector (10), and a position adjustment slide (15), wherein the directional X-ray source (7) and the X-ray detector (10) are respectively installed at both ends of the position adjustment slide (15);

The measuring system comprises a liquid meter (17), a gas meter (18), an electronic balance (11), a vacuum pump (23), a pressure gauge (22), an outlet control valve (19), a vacuum control valve (20), a metering control valve (21) and connecting pipe, and a tee;

The inlet of rock slab holder (8) is respectively connected with the gas cylinder (1) and the water pump (5) by the pipe, the outlet is connected with the liquid meter (17) and the vacuum pump (23) by the tee, and the inlet and outlet are also connected with the differential pressure sensor (9); the rock slab holder (8) is connected with the booster pump (14) through the pipe around; the gas source control valve (2), the gas flow meter (3) and the gas pressure sensor (4) are installed between the gas cylinder (1) and the rock slab holder (8); the liquid pressure sensor (6) is installed between the water pump (5) and the rock slab holder (8); the pressure gauge (13) and the confining pressure control valve (12) are installed between the pressure pump (14) and the rock slab holder (8); the pressure gauge (22) and the vacuum control valve (20) are installed between the vacuum pump (23) and the tee; the metering control valve (21) is installed between the liquid meter (17) and the tee;

The rock slab holder (8) is placed on the electronic balance (11), and both are located between the directional X-ray source (7) and the X-ray detector (10); the inlet of the gas meter (18) is connected with the liquid meter (17), and the outlet is connected with the outlet control valve (19) that is connected to the external atmosphere;

The gas meter (18), the liquid meter (17) and the X-ray detector (10) can automatically record the X-ray projection image and the gas volume and liquid volume at the outflow end synchronously.

A method for measuring relative permeability of shale fractures considering probability distribution, comprising the following steps:

Step 1: Prepare two cuboid shale slabs of the same size (10 cm*10 cm*5 cm), stack them together, and lay 40-70-mesh ceramsite with a concentration of 2.5 kg/m² on the contact surface;

Step 2: Put the whole shale slab into the rock slab holder (8), apply 10 MPa confining pressure on the upper, lower and left and right sides of the slab with the booster pump (14), and measure the mass (denoted as $m_1$) of the complete shale sample with proppant by the electronic balance (11);

Step 3: Turn on the directional X-ray source (7) and adjust CT scanning parameters according to the rock slab size and the fracture size (set the scanning voltage as 140 KV, the power as 10 W, the resolution as 10 um and the exposure time as 1 s, and set the X-ray source 1 cm away from the rock slab inlet and the detector 2 cm away from the rock slab outlet);

Step 4: Determine the attenuation coefficient of pure substance with the scanning parameters set in Step 3, specifically including:

Step 4-1: Determine the air attenuation coefficient;

Depressurize and take out the rock slab in the rock slab holder (8), then inject air into the rock slab holder (8), and pressurize it to the fluid pressure of 5 MPa required for the relative permeability experiment; acquire CT projection images of pure air continuously after the pressure is stabilized, average multiple projection images to obtain the X-ray projection result of pure air, and record it as projection image A;

Step 4-2: Determine the attenuation coefficient of gaseous medium in relative permeability experiment (krypton gas is used in the embodiment for higher contrast ratio);

Depressurize and empty the air in the rock slab holder (8), then inject krypton gas into the rock slab holder (8), and pressurize it to the fluid pressure of 5 MPa required for the relative permeation experiment; acquire the CT projection images of pure gas continuously after the pressure is stabilized, average multiple projection images to obtain the X-ray projection result of pure gas, and record it as projection image B;

Step 4-3: Determine the attenuation coefficient of liquid medium in relative permeability experiment (15% KI solution is used in the embodiment for higher contrast ratio);

Depressurize and empty the air in the rock slab holder (8), then inject 15% KI solution into the rock slab holder (8), and pressurize it to the fluid pressure of 5 MPa required for the relative permeability experiment; acquire the CT projection images of pure liquid continuously after the pressure is stabilized, average multiple projection images to obtain the X-ray projection results of pure liquid, and record it as projection image C;

Step 4-4: Determine the proppant attenuation coefficient;

Depressurize and drain the fluid in the rock slab holder (8), put the standard block made of the same material as the proppant (X length is the same as the internal length of the holder) into the holder, and boost the confining pressure to 5 MPa; acquire the CT projection image continuously after the pressure is stabilized, average multiple projection images to obtain the X-ray projection result of the proppant material, and record it as projection image D;

Step 4-5: Calculate the attenuation coefficient;

X-ray will be attenuated when passing through multiple materials that are uniformly segmented, satisfying the following relationship:

$$\mu_1 x_1 + \mu_2 x_2 + \mu_3 x_4 + L + \mu_n x_n = -\ln \frac{I}{I_0} \quad (1)$$

Where, $\mu_1, \mu_2, \mu_3 \ldots \mu_n$ are the attenuation coefficients of the materials through which the ray passes in turn; $x_1, x_2, x_3 \ldots x_n$ are the thicknesses of the materials through which the ray passes in turn; $I_0$ is the X-ray incident intensity; $I$ is the intensity of X-ray after attenuation;

In the above four sub-steps, the X-ray emitted by the directional X-ray source (7) will pass through the air, the outer wall of the rock slab holder (8), and the substance inside the holder. Except the substance inside the holder, the X-ray attenuation degree on the other paths is the same;

Therefore, under the same scanning conditions, the X-ray intensity attenuation at the corresponding pixel positions in the X-ray projection images A, B, C and D can be expressed as:

$$\mu_{air}L + \sum_i \mu_i x_i = -\ln \frac{I_A}{I_0} \quad (2)$$

$$\mu_{gas}L + \sum_i \mu_i x_i = -\ln \frac{I_B}{I_0} \quad (3)$$

$$\mu_{liquid}L + \sum_i \mu_i x_i = -\ln \frac{I_C}{I_0} \quad (4)$$

$$\mu_{proppant}L + \sum_i \mu_i x_i = -\ln \frac{I_C}{I_0} \quad (5)$$

Where, $\mu_{air}, \mu_{gas}, \mu_{liquid}$ and $\mu_{proppant}$ stand for the attenuation coefficients of X-ray passing through air, experimental gas, experimental liquid and proppant successively; L is the inner length of the X-ray passing through the holder cavity; $I_0$ is the X-ray incident intensity: $I_A, I_B, I_C$ and $I_D$ are the intensity of X-ray attenuation in the projection images A, B, C and D, respectively;

$$\sum_i \mu_i x_i$$

the sum of X-ray attenuation on other paths;

Solve the Equations (2 to 5) simultaneously to obtain:

$$(\mu_{gas} - \mu_{air})L = -\ln \frac{I_B}{I_A} \quad (6)$$

$$(\mu_{liquid} - \mu_{air})L = -\ln \frac{I_C}{I_A} \quad (7)$$

$$(\mu_{proppant} - \mu_{air})L = -\ln \frac{I_D}{I_A} \quad (8)$$

Figure 2:
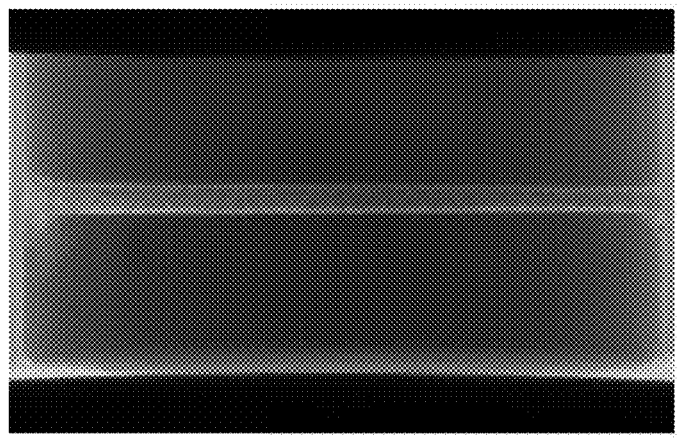
FIG. 2 shows the X-ray projection results shale slabs in initial state.

Where, the $I_A, I_B, I_C$ and $I_D$ of each pixel in the projection images A, B, C and D are known, and the inner length L of the holder cavity is known; therefore, the differences ($\mu_{gas}-\mu_{air}$), ($\mu_{liquid}-\mu_{air}$) and ($\mu_{proppant}-\mu_{air}$) of the attenuation coefficients are obtained respectively;

Step 5: Put the whole shale slab into the rock slab holder (8), and apply 10 MPa confining pressure on the upper, lower and left and right sides of the slab with the booster pump (14); inject air and pressurize to the fluid pressure of 5 MPa required for the relative permeability experiment; acquire the CT projection images continuously after the pressure is stabilized, average multiple projection images to obtain the X-ray projection result of the rock slab, and record it as projection image E, as shown in FIG. 2;

Step 6: Calculate the porosity and pore volume in the propped fractures of the shale rock slab;

When the parallel X-ray passes through the propped fracture, only air and proppant can attenuate it, which can be expressed as:

$$\mu_{air}x_{air} + \mu_{proppant}x_{proppant} + \sum_i \mu_i x_i = -\ln \frac{I_E}{I_0} \quad (9)$$

Solve the Equations (2) and (9) simultaneously to obtain:

$$(\mu_{proppant} - \mu_{air})x_{proppant} = -\ln \frac{I_E}{I_A} \quad (10)$$

Then converse it into porosity-related equation:

$$(\mu_{proppant} - \mu_{air})\phi L = -\ln \frac{I_E}{I_A} \quad (11)$$

Where, all other parameters except porosity $\phi$ are known, so the porosity of each point in the propped fracture can be calculated, and the void volume in the fracture can be calculated by the following equation:

$$V_p = \sum_j A\phi_j L \quad (12)$$

Figure 3:
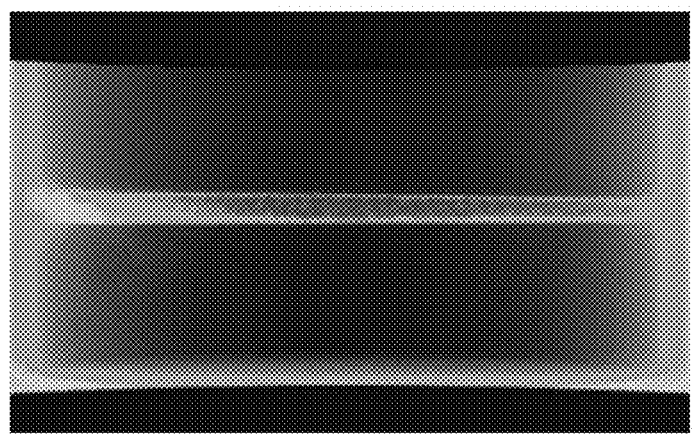
FIG. 3 shows the X-ray projection results of shale slabs with a gas volume fraction of 0.8.

Where, A is the area of a single pixel in the projection image; $\phi_j$ is the calculated porosity at each pixel point; $V_p$ is the void volume in the propped fracture;

Step 7: Turn on the X-ray source and record the projection image every 1 s; then adjust the flow rates of the flow meter (3) and the water pump (5), inject gas and water into the rock slab in a certain proportion (gas volume fraction: 1, 0.8, 0.6, 0.4, 0.2, 0), and record the gas rate $q_g$ at the outlet, the water rate $q_w$, pressure $p_1$ at the holder inlet, the pressure difference $\Delta p$ between the two ends of the rock slab, and the value m of the electronic balance at the corresponding time; keep the proportion of injected gas unchanged for 3 h, and then change the proportion until the gas volume proportion is decreased to 0; the projection image at a gas volume fraction of 0.8 is shown in FIG. 3;

There are 6 gas/water ratios in this step; for each ratio, 3*60*60=10,800 projection images can be acquired, totally 64,800 images, and the gas volume at the outlet, the water rate, pressure at the holder inlet, the pressure difference between the two ends of the rock slab, and the value of the electronic balance are also recorded;

Step 8: Calculate the saturation and permeability at each moment with under various gas-water injection ratio;

During gas and water injection, when the parallel X-ray passes through the propped fracture, its intensity attenuation can be expressed as:

$$\mu_{gas}x_{gas} + \mu_{proppant}x_{proppant} + \mu_{liquid}x_{liquid} + \sum_i \mu_i x_i = -\ln \frac{I_t}{I_0} \quad (13)$$

Solve the Equations (3) and (13) simultaneously to obtain:

$$(\mu_{proppant} - \mu_{gas})x_{proppant} + (\mu_{liquid} - \mu_{gas})x_{liquid} = -\ln \frac{I_t}{I_B} \quad (14)$$

Then converse it into saturation-related equation:

$$[(\mu_{proppant} - \mu_{gas})(1 - \phi) + (\mu_{liquid} - \mu_{gas})\phi s_w]L = -\ln \frac{I_t}{I_B} \quad (15)$$

Where, all other parameters except saturation $S_w$ are known; the water saturation at each position in the propped fracture at the corresponding time can be calculated according to the X-ray projection results obtained at each time. The overall water saturation in the fracture at each time is calculated by the following equation:

$$\overline{s_w} = \frac{V_w}{V_p} = \frac{\sum_j A\phi_j s_{wj} L}{\sum_j A\phi_j L} = \frac{\sum_j \phi_j s_{wj}}{\sum_j \phi_j} \quad (16)$$

The mass of water imbibed into matrix at each time can be calculated by the following equation:

$$m_w = m - m_1 - \rho \sum_j A\phi_j s_{wj} L \quad (17)$$

Effective permeability of gas and water at corresponding time:

$$K_{ge} = \frac{2p_a \cdot q_g \cdot \mu_g \cdot l}{A(p_1^2 - p_a^2)} \quad (18)$$

$$K_{we} = \frac{q_w \cdot \mu_w \cdot l}{A\Delta p} \quad (19)$$

Where, $K_{ge}$ is the effective permeability of gas; $K_{we}$ is the effective permeability of liquid; $p_a$ is atmospheric pressure; $p_1$ is the pressure at the inlet; $q_g$ is gas flow rate; $q_w$ is liquid flow rate; l is the length of propped fracture; A is the sectional area of the fracture; $\mu_g$ and $\mu_w$ are gas and liquid viscosity at the test temperature and pressure, respectively;

Then calculate the relative permeability of gas and water according to Equations (18) and (19):

$$K_{rg} = \frac{K_{ge}}{K_g} \quad (20)$$

$$K_{rw} = \frac{K_{we}}{K_g} \quad (21)$$

Figure 4:
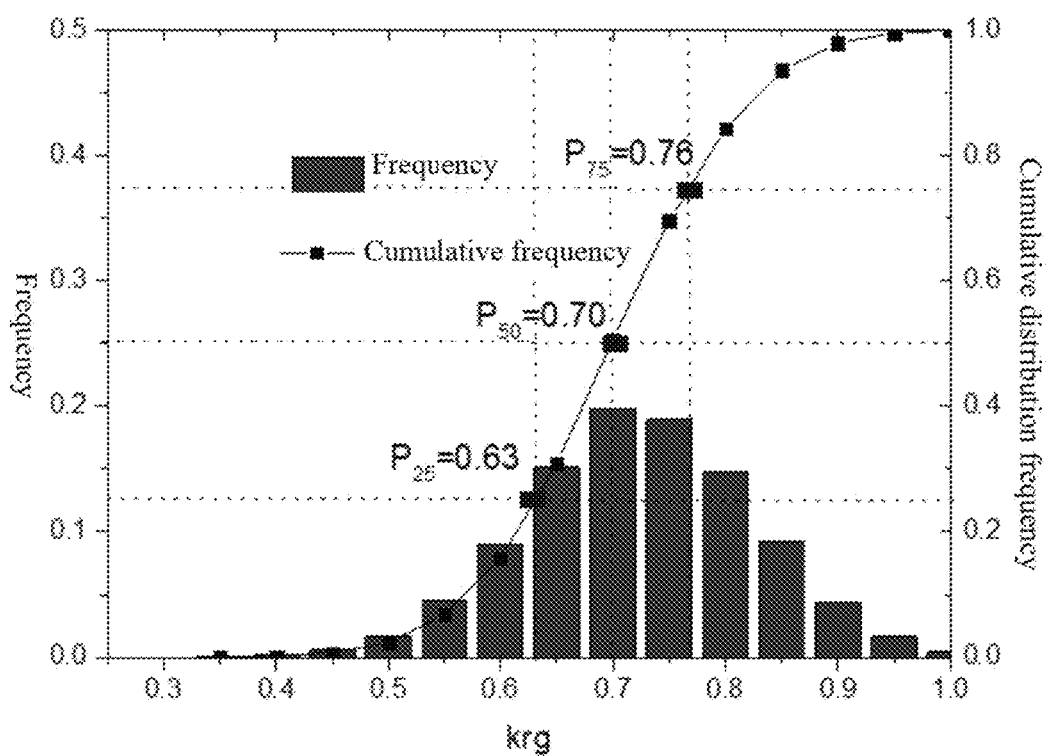
FIG. 4 is a frequency distribution diagram of gas relative permeability when the water saturation is 0.2.
Figure 5:
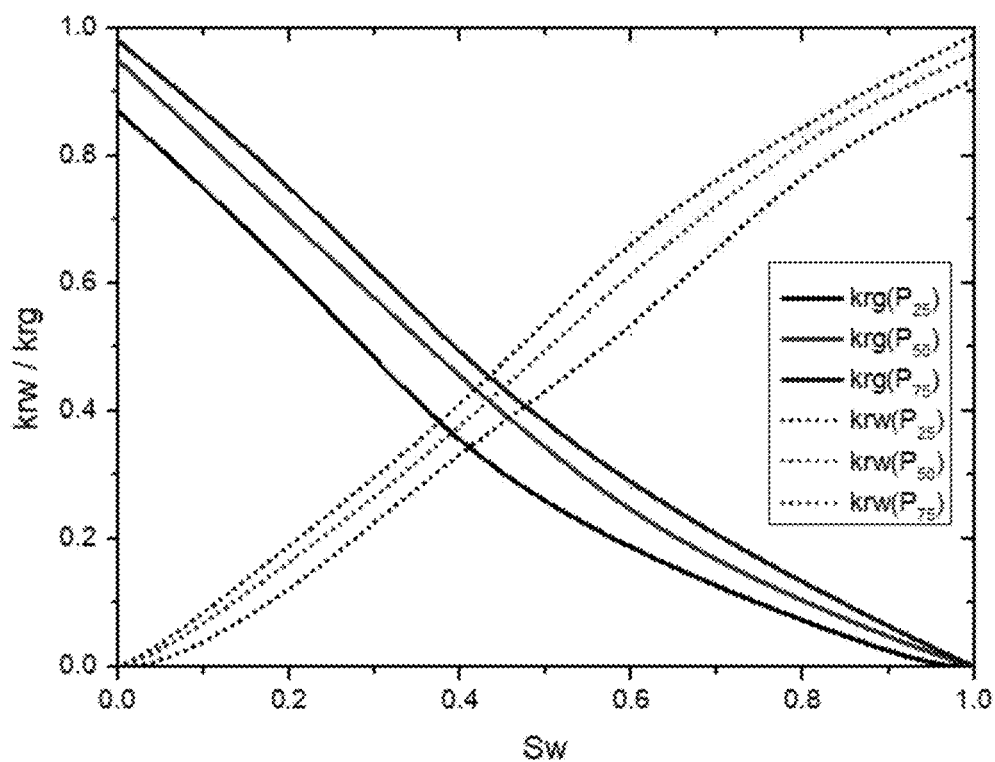
FIG. 5 is the curve of fracture relative permeability considering probability distribution.

Where, $K_g$ is the effective permeability of pure gas; $k_{rg}$ and $k_{rw}$ are the relative permeability of gas and water respectively;

in this way, the water saturation $\overline{s_w}$ and relative permeability values $K_{rg}$ and $K_{rw}$ of proppant fractures at different times can be obtained; as the flow of gas and water in propped fractures may not satisfy the Darcy law and local turbulence may occur, the water saturation $\overline{s_w}$ may be different at different times even though the proportion of injected gas is same; additionally, with the same water saturation $\overline{s_w}$, the relative permeability values $K_{rg}$ and $K_{rw}$ of gas and water may be inconsistent; it can be seen from Step 7 that 10,800 projection images can be acquired at each gas/water ratio, and there should be 10,800 different average water saturations obtained; even if with the same water saturation, the relative permeability calculated according to flow and pressure is not completely the same; in order to consider the unstable condition, the relative permeability curve of the fracture is characterized by $R^{th}$ percentile;

Step 9: Calculate the fracture relative permeability curve considering the probability distribution;

Step 9-1: Count the gas phase relative permeability value $K_{rg}(\overline{s_w})$ corresponding to the same water saturation $\overline{s_w}$ at all times, and work out a frequency distribution histogram at $K_{rg}(\overline{s_w})$, as shown in FIG. 4; calculate the gas relative permeability values corresponding to the first quartile ($P_{25}$), the second quartile ($P_{50}$) and the third percentile ($P_{75}$); similarly, work out the water relative permeability values corresponding to the first quartile ($P_{25}$), the second quartile ($P_{50}$) and the third percentile ($P_{75}$);

Step 9-2: Repeat Step 9-1 with different water saturation $\overline{s_w}$, and count the relative permeability values of gas and water corresponding to each $R^{th}$ percentile at different water saturations;

Step 9-3: Based on the relative permeability values of gas and water corresponding to different water saturations under the same $R^{th}$ percentile, the fracture relative permeability curve considering probability distribution can be obtained, as shown in FIG. 5.

The above are not intended to limit the present invention in any form. Although the present invention has been disclosed as above with preferred embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A method for measuring the relative permeability of propped fractures in shale considering probability distribution, comprising using a device for measuring the relative permeability of propped fractures in shale considering probability distribution, comprising a displacement system, a CT scanning imaging system and a metering system; wherein
the displacement system comprises a gas cylinder (1), a water pump (5), a booster pump (14), a rock slab holder (8), and a differential pressure sensor (9); the CT scanning imaging system comprises a directional X-ray source (7), an X-ray detector (10), and an X-ray shielding box (16); the metering system comprises a tee, a liquid meter (17), a gas meter (18), an electronic balance (11), and a vacuum pump (23);
an inlet of the rock slab holder (8) is respectively connected with the gas cylinder (1) and the water pump (5) by a pipe, an outlet of the rock slab holder is connected with the liquid meter (17) and the vacuum pump (23) by the tee, and the differential pressure sensor (9) is connected with both ends of the rock slab holder (8); the booster pump (14) is connected with the rock slab holder (8) by the pipe;
the directional X-ray source (7), the X-ray detector (10), the rock slab holder (8), and the electronic balance (11) are all placed in the X-ray shielding box (16), the rock slab holder (8) is placed on the electronic balance (11) and located between the directional X-ray source (7) and the X-ray detector (10);
an inlet of the gas meter (18) is connected with the liquid meter (17), and an outlet of the gas meter is connected to the external atmosphere;
a gas source control valve (2), a gas flow meter (3) and a gas pressure sensor (4) are installed between the gas cylinder (1) and the rock slab holder (8);
the method specifically comprising the following steps:

Step 1: preparing two cuboid shale slabs of the same size, stacking them together, and laying proppants on the contact surface of the stacked slabs to form a whole shale slab;

Step 2: putting the whole shale slab into the rock slab holder (8), applying confining pressure on the upper, lower, left and right sides of the whole shale slab with the booster pump (14), and measuring the mass (denoted as $m_1$) of the whole shale slab with proppant by the electronic balance (11);

Step 3: turning on the directional X-ray source (7), adjusting CT scanning parameters according to a shale rock slab size and a fracture size and determining a set of appropriate scanning parameters;

Step 4: determining the attenuation coefficient of pure substance with the scanning parameters set in Step 3; filling the rock slab holder (8) with air and pressurizing to a specified fluid pressure acquiring CT projection images of pure air continuously after the pressure is stabilized; averaging multiple projection images to obtain the X-ray projection result of pure air, which is denoted as projection image A; then, conducting the same measurement for the gas and liquid used in relative permeability test and a standard block made of the same material as the proppant respectively to obtain the corresponding X-ray projection results, denoted as projection image B, projection image C and projection image D respectively; then, calculating the difference of attenuation coefficients of pure substances by the following equation;

$$(\mu_{gas} - \mu_{air})L = -\ln\frac{I_B}{I_A}$$

$$(\mu_{liquid} - \mu_{air})L = -\ln\frac{I_C}{I_A}$$

$$(\mu_{proppant} - \mu_{air})L = -\ln\frac{I_D}{I_A}$$

where $I_A$, $I_B$, $I_C$ and $I_D$ are the intensity of each pixel point in the projection images A, B, C and D, respectively; L is the inner length of the holder cavity of the rock slab holder; $\mu_{air}$, $\mu_{gas}$, $\mu_{liquid}$ and $\mu_{proppant}$ stand for the attenuation coefficients of X-ray passing through air, experimental gas, experimental liquid and proppant successively;

Step 5: putting the whole shale slab into the rock slab holder (8), and applying confining pressure on the upper, lower, left and right sides of the slab with the booster pump (14); injecting air and pressurizing to the fluid pressure p required for the relative permeability experiment;
acquiring the CT projection images continuously after the pressure is stabilized, averaging multiple projection images to obtain the X-ray projection result of the rock slab, denoted as projection image E;

Step 6: calculating the porosity and pore volume in the propped fractures of the shale rock slab;

$$(\mu_{proppant} - \mu_{air})\phi L = -\ln\frac{I_E}{I_A}$$

where L is the inner length of the holder cavity of the rock slab holder; φ is the porosity; $I_E$ is the intensity of each pixel point in the projected image E;

$$V_p = \sum_j A\phi_j L$$

where A is the area of a single pixel in the projection image; $\phi_j$ is the calculated porosity at each pixel point; $V_p$ is the pore volume in the propped fracture;

Step 7: turning on the directional X-ray source (7) and recording projected images per second; adjusting the flow rates of the flow meter (3) and the water pump (5), injecting gas and water into the whole shale slab in a certain proportion, and recording the following data per second for a period of time: projection image of the whole shale slab, the gas rate $q_s$ at the holder outlet, the water rate $q_w$, pressure $p_1$ at the holder inlet, the pressure difference $\Delta_p$ between the two ends of the whole shale slab, and the value m of the electronic balance; maintaining the injection process of each ratio for the same time and changing another ratio until the gas volume ratio drops to 0;

Step 8: calculating the saturation and permeability at each moment under various gas-water injection ratio; wherein the water saturation at each pixel point in the projection image at each moment is calculated by the following equation:

$$[(\mu_{proppant} - \mu_{gas})(1-\phi) + (\mu_{liquid} - \mu_{gas})\phi s_w]L = -\ln\frac{I_t}{I_B}$$

the overall average water saturation in the fracture is calculated by the following equation:

$$\overline{s_w} = \frac{V_w}{V_p} = \frac{\sum_j A\phi_j s_{wj} L}{\sum_j A\phi_j L} = \frac{\sum_j \phi_j s_{wj}}{\sum_j \phi_j}$$

the mass of water imbibed into matrix is calculated by the following equation:

$$m_w = m - m_1 - \rho \sum_j A\phi_j s_{wj} L$$

effective permeabilities of gas and water at corresponding time are calculated by the following equation:

$$K_{ge} = \frac{2p_a \cdot q_g \cdot \mu_g \cdot l}{A(p_1^2 - p_a^2)}$$

$$K_{we} = \frac{q_w \cdot \mu_w \cdot l}{A\Delta p}$$

where, $K_{ge}$ is the effective permeability of gas; $K_{we}$ is the effective permeability of liquid; $p_a$ is atmospheric pressure; $p_1$ is the pressure at the inlet; $q_g$ is gas flow rate; $q_w$ is liquid flow rate; l is the length of propped fracture; A is the sectional area of the fracture; $\mu_g$ and $\mu_w$ are gas and liquid viscosity at the test temperature and pressure, respectively;

the relative permeabilities of gas and water are calculated by the following equation:

$$K_{rg} = \frac{K_{ge}}{K_g}$$

$$K_{rw} = \frac{K_{we}}{K_g}$$

where, $K_g$ is the effective permeability of pure gas; $k_{rg}$ and $k_{rw}$ are the relative permeability of gas and water respectively; and Step 9: calculating a fracture relative permeability curve considering the probability distribution according to the saturation and permeability at each time;

wherein Step 9 specifically comprises:

Step 91: counting the gas phase relative permeability value $K_{rg}$ under the same water saturation $\overline{s_w}$ at all times, and working out a frequency distribution histogram of $K_{rg}$; calculating the gas relative permeability values corresponding to a $R^{th}$ percentile; similarly, working out the water relative permeability values corresponding to the $R^{th}$ percentile;

Step 92: repeating Step 91 with different water saturation $\overline{s_w}$ and counting the relative permeability values of gas and water phases corresponding to each $R^{th}$ percentile at different water saturations; and Step 93: based on the relative permeability values of gas and water phases corresponding to different water saturations under the same $R^{th}$ percentile, obtaining the fracture relative permeability curve considering probability distribution.

2. The method for measuring the relative permeability of propped fractures in shale considering probability distribution according to claim 1, wherein a liquid pressure sensor (6) is installed between the water pump (5) and the rock slab holder (8).

3. The method for measuring the relative permeability of propped fractures in shale considering probability distribution according to claim 1, wherein a pressure gauge I (13) and a confining pressure control valve (12) are installed between the pressure pump (14) and the rock slab holder (8).

4. The method for measuring the relative permeability of propped fractures in shale considering probability distribution according to claim 1, wherein a pressure gauge II (22) and a vacuum control valve (20) are installed between the vacuum pump (23) and the tee.

5. The method for measuring the relative permeability of propped fractures in shale considering probability distribution according to claim 1, wherein a metering control valve (21) is installed between the liquid meter (17) and the tee.

6. The method for measuring the relative permeability of propped fractures in shale considering probability distribution according to claim 1, wherein an outlet control valve (19) is installed at the outlet of the gas meter (18).

7. The method for measuring the relative permeability of propped fractures in shale considering probability distribution according to claim 1, wherein a position adjustment slide (15) is also installed in the X-ray shielding box (16), and the directional X-ray source (7) and the X-ray detector (10) are respectively installed at both ends of the position adjustment slide (15).

* * * * *